(12) United States Patent
Falkenstein et al.

(10) Patent No.: US 8,796,419 B2
(45) Date of Patent: Aug. 5, 2014

(54) HYDROPHOBIC INTERACTION CHROMATOGRAPHY METHOD

(75) Inventors: Roberto Falkenstein, Munich (DE); Nicole Fuehrler, Schlehdorf (DE); Maria Smida, Oberding (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/697,406

(22) PCT Filed: May 17, 2011

(86) PCT No.: PCT/EP2011/057960
§ 371 (c)(1),
(2), (4) Date: Nov. 12, 2012

(87) PCT Pub. No.: WO2011/144606
PCT Pub. Date: Nov. 24, 2011

(65) Prior Publication Data
US 2013/0059336 A1  Mar. 7, 2013

(30) Foreign Application Priority Data

May 19, 2010 (EP) ..................... 10163273
Oct. 27, 2010 (EP) ..................... 10188972

(51) Int. Cl.
*C07K 1/20* (2006.01)
*C12P 21/00* (2006.01)
(52) U.S. Cl.
USPC ........................................ 530/344; 435/69.1
(58) Field of Classification Search
None
See application file for complete search history.

(56) References Cited

U.S. PATENT DOCUMENTS

| 6,005,082 A | 12/1999 | Smeds |
| 2004/0152076 A1 | 8/2004 | Willson et al. |
| 2007/0037966 A1 | 2/2007 | Rasmussen et al. |

FOREIGN PATENT DOCUMENTS

| WO | 94/07912 | 4/1994 |
| WO | 98/06739 | 2/1998 |
| WO | 02/37100 | 5/2002 |
| WO | 2004036189 | 4/2004 |
| WO | 2005/035092 | 4/2005 |
| WO | 2008/025527 | 3/2008 |

OTHER PUBLICATIONS

Mateo C et al., Journal of Chromatography (XP004233627), A 915:97-106 (Apr. 27, 2001).
(International Search Report PCT/EP2011/057960 Sep. 7, 2011).
The Japanese Office Action, issued on Apr. 14, 2014, in the corresponding Japanese application No. 2013-508524.

*Primary Examiner* — Samuel Woolwine
*Assistant Examiner* — Kaijiang Zhang

(57) ABSTRACT

Herein is reported a method for purifying a polypeptide comprising a histidine-tag comprising the steps of i) applying a solution comprising the polypeptide with a histidine-tag to a hydrophobic interaction chromatography material, and ii) recovering the polypeptide comprising a histidine-tag with a solution comprising imidazole or an imidazole-derivative and thereby purifying the polypeptide comprising a histidine-tag, wherein the solution comprising the polypeptide applied to the hydrophobic interaction chromatography material is free of imidazole or an imidazole-derivative and the polypeptide adsorbed to the hydrophobic interaction chromatography material is recovered with a solution comprising imidazole or an imidazole-derivative.

12 Claims, 11 Drawing Sheets

HYDROPHOBIC INTERACTION CHROMATOGRAPHY METHOD

PRIORITY TO RELATED APPLICATION(S)

This application claims the benefit of European Patent Application No. 10163273.5 filed May 19, 2010, European Patent Application No. 10188972.3 filed Oct. 27, 2010 and International Patent Application PCT/EP2011/057960, filed May 17, 2011. The entire contents of the above-identified applications are hereby incorporated by reference.

Herein is reported a hydrophobic interaction chromatography method for the purification of polypeptides comprising a histidine-tag by elution of the polypeptide from the chromatography material with a solution comprising imidazole or an imidazole-derivative.

BACKGROUND OF THE INVENTION

Proteins play an important role in today's medical portfolio. Expression systems for the production of recombinant polypeptides are well-known in the state of the art. Polypeptides for use in pharmaceutical applications are mainly produced in prokaryotic cells, such as E. coli, and mammalian cells such as CHO cells, NSO cells, Sp2/0 cells, COS cells, HEK cells, BHK cells, PER.C6® cells, and the like.

For human application every pharmaceutical substance has to meet distinct criteria. To ensure the safety of biopharmaceutical agents to humans, for example, nucleic acids, viruses, and host cell proteins, which would cause severe harm, have to be removed. To meet the regulatory specification one or more purification steps have to follow the manufacturing process. Among other, purity, throughput, and yield play an important role in determining an appropriate purification process.

Different methods are well established and widespread used for protein purification, such as affinity chromatography with microbial proteins (e.g. protein A or protein G affinity chromatography), ion exchange chromatography (e.g. cation exchange (sulfopropyl or carboxymethyl resins), anion exchange (amino ethyl resins) and mixed-mode ion exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (see e.g. Vijayalakshmi, M. A., Appl. Biochem. Biotech. 75 (1998) 93-102).

Mateo, C., et al. report about the affinity chromatography of polyhistidine-tagged enzymes (J. Chrom. 915 (2001) 97-106). In WO 02/37100 novel applications of nickel nitrilotriacetic acid (NI-NTA) resin are reported. Methods and kits for purifying his-tagged proteins are reported in WO 2005/035092. In WO 98/06739 a method for the purification of recombinant proteins is reported.

Affinity purification methods involving amino acid mimetics as elution agents are reported in WO 94/07912. In US 2004/0152076 nucleic acid separation using immobilized metal affinity chromatography. A process for the purification of factor VIII is reported in U.S. Pat. No. 6,005,082. In US 2007/0037966 a hydrophobic interaction chromatography purification of factor VII polypeptides is reported.

SUMMARY OF THE INVENTION

It has been found that a polypeptide comprising a histidine-tag can be recovered from a hydrophobic interaction chromatography material with a solution comprising imidazole or an imidazole-derivative. With the method as reported herein recovering solutions comprising organic solvents, such as 2-propanol, can be avoided without loss of selectivity and yield.

Thus, herein is reported a method for obtaining or purifying a polypeptide comprising a histidine-tag comprising the following steps:
applying a first solution comprising the polypeptide with a histidine-tag to a hydrophobic interaction chromatography material, and
recovering the polypeptide comprising a histidine-tag from the hydrophobic interaction chromatography material by applying a second solution comprising imidazole or an imidazole-derivative and thereby obtaining or purifying the polypeptide comprising a histidine-tag.

Herein is also reported a method for producing a polypeptide comprising a histidine-tag comprising the following steps:
cultivating a prokaryotic or eukaryotic cell comprising a nucleic acid encoding a polypeptide comprising a histidine-tag,
recovering the polypeptide comprising a histidine-tag from the cells or/and the cultivation medium, optionally in form of inclusion bodies,
optionally solubilizing and/or re-folding the polypeptide comprising a histidine-tag,
purifying the solubilized and/or re-folded polypeptide comprising a histidine-tag with a hydrophobic interaction chromatography method and thereby producing a polypeptide comprising a histidine-tag.

In one embodiment the hydrophobic interaction chromatography material comprises a matrix of agarose to which hydrophobic ligands have been attached. In another embodiment the ligand is selected from n-, iso- or neo-aliphatic or oligo alkylene glycols. In a further embodiment the ligand is selected from propyl-, butyl-, pentyl-, hexyl-, heptyl-, octyl-, poly (ethylene glycol)-, and poly (propylene glycol)-groups. In a further embodiment the ligand is a phenyl-ligand and the second solution in the recovering step comprises in addition to the imidazole or the imidazole-derivative 2-propanol.

DETAILED DESCRIPTION OF THE INVENTION

Herein is reported a scalable hydrophobic interaction chromatography method operated in bind-and-elute mode for the purification of polypeptides comprising a histidine-tag wherein the recovering of the polypeptide from the hydrophobic interaction chromatography material is with a solution comprising imidazole or an imidazole derivative, such as histidine. By using this elution system, the implementation of elution buffers containing organic solvents like 2-propanol can be avoided, without loss of selectivity and yield.

The terms "applying to" and grammatical equivalents thereof denote a partial step of a purification method in which a solution containing a substance of interest to be purified is brought in contact with a stationary phase. This denotes that a) the solution is added to a chromatographic device in which the stationary phase is located, or b) that a stationary phase is added to the solution comprising the substance of interest. In case a) the solution containing the substance of interest to be purified passes through the stationary phase allowing for an interaction between the stationary phase and the substances in solution. Depending on the conditions, such as e.g. pH, conductivity, salt concentration, temperature, and/or flow rate, some substances of the solution are bound to the stationary phase and, thus, are removed from the solution. Other substances remain in solution. The substances remaining in solution can be found in the flow-through. The "flow-through" denotes the solution obtained after the passage of the chromatographic device irrespective of its origin. It can either be the applied solution containing the substance of interest or the buffer, which is used to flush the column or which is used to cause the elution of one or more substances bound to the stationary phase. In one embodiment the chromatographic device is a column, or a cassette. The substance of interest can be recovered from the solution after the purification step by methods familiar to a person of skill in the art, such as e.g. precipitation, salting out, ultrafiltration, diafiltration, lyophilization, affinity chromatography, or solvent volume reduction to obtain the substance of interest in purified or even substantially homogeneous form. In case b) the stationary phase is added, e.g. as a solid, to the solution containing the substance of interest to be purified allowing for an interaction between the stationary phase and the substances in solution. After the interaction the stationary phase is removed, e.g. by filtration, and the substance of interest is either bound to the stationary phase and removed therewith from the solution or the substance of interest is not bound to the stationary phase and remains in the solution.

The term "buffered" as used within this application denotes a solution in which changes of pH due to the addition or release of acidic or basic substances is leveled by a buffer substance. Any buffer substance resulting in such an effect can be used. In one embodiment the buffer substance is selected from phosphoric acid or salts thereof, acetic acid or salts thereof, citric acid or salts thereof, morpholine, 2-(N-morpholino) ethanesulfonic acid or salts thereof, imidazole or salts thereof, histidine or salts thereof, glycine or salts thereof, or tris (hydroxymethyl) aminomethane (TRIS) or salts thereof. In one embodiment the buffer substance is selected from imidazole or salt thereof or histidine or salts thereof. Optionally the buffered solution may also comprise an additional inorganic salt. In one embodiment the inorganic salt is selected from sodium chloride, sodium sulphate, potassium chloride, potassium sulfate, sodium citrate, and potassium citrate.

A "polypeptide" is a polymer consisting of amino acids joined by peptide bonds, whether produced naturally or synthetically. Polypeptides of less than about 20 amino acid residues may be referred to as "peptides", whereas molecules consisting of two or more polypeptides or comprising one polypeptide of more than 100 amino acid residues may be referred to as "proteins". A polypeptide may also comprise non-amino acid components, such as carbohydrate groups, metal ions, or carboxylic acid esters. The non-amino acid components may be added by the cell, in which the polypeptide is expressed, and may vary with the type of cell. Polypeptides are defined herein in terms of their amino acid backbone structure or the nucleic acid encoding the same. Additions such as carbohydrate groups are generally not specified, but may be present nonetheless.

The term "bind-and-elute mode" denotes a way to perform a chromatography purification method. Herein a solution containing a polypeptide of interest to be purified is applied to a stationary phase, particularly a solid phase, whereby the polypeptide of interest interacts with the stationary phase and is retained thereon. Substances not of interest are removed with the flow-through or the supernatant, respectively. The polypeptide of interest is afterwards recovered from the stationary phase in a second step by applying an elution solution.

The term "polypeptide in monomeric form" denotes a polypeptide not associated with a second polypeptide molecule, i.e. which is neither covalently nor non-covalently bound to another polypeptide molecule either of the same kind or of a different kind. The term "polypeptide in aggregated form" denotes a polypeptide which is associated, either covalently or non-covalently, with at least one additional polypeptide, and which is eluted in a single peak from a size exclusion chromatography column. The term "in monomeric form" not necessarily denotes that 100% (as determined by size exclusion chromatography) of a polypeptide is present in monomeric form. It furthermore denotes that a polypeptide is essentially in monomeric form, i.e. at least 90% (as determined by size exclusion chromatography) of the polypeptide are in monomeric from, or at least 95% of the polypeptide are in monomeric form, or at least 98% of the polypeptide are in monomeric form, or at least 99% of the polypeptide are in monomeric form, or particularly more than 99% (as determined by size exclusion chromatography) of the polypeptide are in monomeric form. The term "in monomeric and in aggregated form" denotes a mixture of polypeptide molecules not associated with other polypeptide molecules and of polypeptide molecules associated with other polypeptide molecules. In this mixture neither of the monomeric form nor the aggregated form is present exclusively.

The term "inclusion body" denotes a dense intracellular mass of aggregated polypeptide of interest, which constitutes a significant portion of the total cell protein, including all cell components of a prokaryotic cell.

The term "denaturized" denotes forms of polypeptides wherein these have a secondary, tertiary, and/or quaternary structure that is not the native one. The polypeptide in this non-native form may be soluble but concomitantly in a biologically inactive conformation. Or the polypeptide may be insoluble and in a biologically inactive conformation with e.g. mismatched or unformed disulfide bonds. This insoluble polypeptide can be, but need not be, contained in inclusion bodies.

The term "refolded" refers to a polypeptide obtained from a denaturized form. Typically, the goal of refolding is to produce a protein having a higher level of activity than the protein would have if produced without a refolding step. A folded protein molecule is most stable in the conformation that has the least free energy. Most water soluble proteins fold in a way that most of the hydrophobic amino acids are in the interior part of the molecule, away from the water. The weak bonds that hold a protein together can be disrupted by a number of treatments that cause a polypeptide to unfold, i.e. to denaturize. A folded protein is the product of several types of interactions between the amino acids themselves and their environment, including ionic bonds, Van der Waals interactions, hydrogen bonds, disulfide bonds and covalent bonds.

The terms "denatured" or "denaturized" as used herein refer to a polypeptide in which ionic and covalent bonds and Van der Waals interactions which exist in the molecule in its native or refolded state are disrupted. Denaturation of a polypeptide can be accomplished, for example, by treatment with 8 M urea, reducing agents such as mercaptoethanol, heat, pH, temperature and other chemicals. Reagents such as 8 M urea disrupt both the hydrogen bonds and the hydrophobic bonds, and if mercaptoethanol is also added, the disulfide bridges (S—S) which are formed between cysteines are reduced to two —S—H groups. Refolding of polypeptides which contain disulfide linkages in their native or refolded state may also involve the oxidation of the —S—H groups present on cysteine residues for the protein to reform the disulfide bonds.

Generally, the position of a hydrophobic interaction chromatography is variable in a multi step purification sequence of a polypeptide.

Methods for purifying polypeptides are well established and widespread used. They are employed either alone or in combination. Such methods are, for example, affinity chromatography using thiol ligands with complexed metal ions (e.g. with Ni(II)- and Cu(II)-affinity material) or microbial-derived proteins (e.g. protein A or protein G affinity chromatography), ion exchange chromatography (e.g. cation exchange (carboxymethyl resins), anion exchange (amino ethyl resins) and mixed-mode exchange chromatography), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), size exclusion chromatography, and preparative electrophoretic methods (such as gel electrophoresis, capillary electrophoresis).

The purification process of immunoglobulins in general comprises a multistep chromatographic part. In the first step non-immunoglobulin polypeptides and proteins are separated from the immunoglobulin fraction by an affinity chromatography, e.g. with protein A. Afterwards an ion exchange chromatography can be performed to disunite the individual immunoglobulin classes and to remove traces of protein A, which has been coeluted from the first column. Finally a third chromatographic step is necessary to separate immunoglobulin monomers from multimers and fragments of the same class. Sometimes the amount of aggregates is high (5% or more) and it is not possible to separate them efficiently in the third purification step necessitating further purification steps.

It has been found that a polypeptide comprising a histidine-tag can be recovered from a hydrophobic interaction chromatography material with a solution comprising imidazole or an imidazole-derivative. This finding was very surprising as imidazole or imidazole-derivatives are generally used to recover histidine-tagged polypeptides from metal affinity chromatography materials but not from hydrophobic interaction chromatography materials. By using metal affinity chromatography materials it is not possible to discriminate between correctly folded, aggregated, partially folded, and unfolded polypeptide forms as all these different forms comprise a histidine-tag and bind to the metal affinity chromatographic material. However, it has been found that by using a hydrophobic interaction chromatography material it is possible to resolve these closely related polypeptide forms. At the same time this chromatography material has sufficient binding capacity for industrial production scale separations.

Therefore, herein is reported as a first aspect a method for purifying a polypeptide that has a histidine-tag comprising the following steps:
applying a solution comprising the polypeptide with a histidine-tag to a hydrophobic interaction chromatography material, and
recovering the polypeptide comprising a histidine-tag with a solution comprising imidazole or an imidazole-derivative and thereby purifying the polypeptide comprising a histidine-tag.

As the imidazole or imidazole-derivative is used for the recovery of the bound polypeptide the solution comprising the polypeptide which is applied to the hydrophobic interaction chromatography material is free of imidazole and of any imidazole-derivative. The polypeptide retained on the hydrophobic interaction chromatography material is recovered with a solution comprising imidazole or an imidazole-derivative. This method is operated in the bind-and-elute mode, i.e. the polypeptide comprising a histidine-tag is first bound to the hydrophobic interaction chromatography material and thereafter, in a further step, recovered from the hydrophobic interaction chromatography material. Intermittent wash steps can be included in the methods as reported herein. In these wash steps the applied solution(s) is(are) free of imidazole and imidazole derivatives.

In the method as reported herein all solutions are free of, i.e. do not contain, imidazole or an imidazole-derivative except for the solution for recovering the polypeptide comprising a histidine-tag from the hydrophobic interaction chromatography material. In one embodiment the solution comprising imidazole or an imidazole-derivative is an aqueous solution. In a further embodiment the solution comprising imidazole or an imidazole-derivative does not comprise, i.e. it is free of, an organic solvent and/or an aliphatic alcohol. In a further embodiment the solution comprising imidazole or an imidazole-derivative is consisting of water, imidazole or an imidazole-derivative, a buffer substance, and optionally one or two or three inorganic salts.

The term "imidazole or an imidazole-derivative" denotes a compound selected from imidazole, substituted imidazole, histidine, and histidine-derivatives. In one embodiment the imidazole or imidazole-derivative is selected from imidazole and histidine.

The hydrophobic interaction chromatography material in one embodiment comprises a matrix of agarose to which a hydrophobic ligand has been covalently linked. In a further embodiment the ligand is an n-, iso- or neo-aliphatic ligand, or an oligo (alkylene glycol)-ligand. In a further embodiment the ligand is a propyl-, butyl-, pentyl-, hexyl-, heptyl-, octyl-, poly (ethylene glycol)-, or poly (propylene glycol)-ligand. In one embodiment the ligand is a poly (propylene glycol)-ligand. In another embodiment the ligand is a phenyl-ligand and the solution in the recovering step comprises in addition 2-propanol.

The terms "comprising a histidine-tag" or "histidine-tagged" denote the presence of a consecutive sequence of histidine residues either at the C-terminus or at the N-terminus of a polypeptide. The histidine-tag may be directly at the respective terminus or at maximum within up to 10 residues of the respective terminus. The number of histidine residues in a histidine-tag is of from 3 residues up to 10 residues, i.e. 3, or 4, or 5, or 6, or 7, or 8, or 9, or 10 residues. In one embodiment the number of histidine residues is of from 4 residues up to 8 residues.

In one embodiment of the aspects as reported herein the method for purifying or obtaining a polypeptide comprising a histidine-tag comprises the following steps:
applying a first solution to the hydrophobic interaction chromatography material to produce a conditioned hydrophobic interaction chromatography material,
applying a second solution comprising the polypeptide comprising a histidine-tag to the conditioned hydrophobic interaction chromatography material,
optionally applying a third solution to the hydrophobic interaction chromatography material,
recovering and thereby purifying or obtaining the polypeptide with a fourth solution comprising imidazole or an imidazole-derivative from the hydrophobic interaction chromatography material.

The first to third solutions are free of imidazole and any imidazole-derivative.

Polypeptides comprising a histidine-tag can be produced recombinantly in eukaryotic and prokaryotic cells, such as CHO cells, HEK cells and *E. coli*. If the polypeptide is produced in prokaryotic cells it is generally obtained in the form of insoluble inclusion bodies. The inclusion bodies can easily be recovered from the prokaryotic cell and the cultivation medium. The polypeptide obtained in insoluble form in the inclusion bodies has to be solubilized before a purification and/or re-folding procedure can be carried out. Generally metal affinity chromatography is not able to discriminate between correctly folded, aggregated, partially folded and unfolded polypeptide forms contained in a solution e.g. obtained after solubilization and/or re-folding. This is due to the fact that the different polypeptide forms all comprise a histidine-tag, which is responsible for the interaction with the metal affinity chromatography material. It has been found that a hydrophobic interaction chromatography material can separate these different but closely related polypeptide forms when an imidazole or imidazole-derivative containing solution is employed for recovery. This finding was absolutely unexpected, as imidazole and imidazole-derivatives are generally used to recover polypeptides comprising a histidine-tag from chelating chromatography materials. The control with a polypeptide lacking a histidine-tag showed that the effect of imidazole induced recovery was specific for the polypeptide comprising a histidine tag.

Thus, a second aspect as reported herein is a method for producing a polypeptide comprising a histidine-tag comprising the following steps:
    cultivating a prokaryotic or eukaryotic cell comprising a nucleic acid encoding a polypeptide comprising a histidine-tag,
    recovering the polypeptide comprising a histidine-tag from the prokaryotic or eukaryotic cells or/and the cultivation medium, optionally in form of inclusion bodies in case of prokaryotic cells,
    optionally solubilizing and/or re-folding the polypeptide comprising a histidine-tag,
    purifying the polypeptide comprising a histidine-tag with a hydrophobic interaction chromatography method as reported herein and thereby producing a polypeptide comprising a histidine-tag.

In one embodiment the hydrophobic interaction chromatography method comprises the following steps:
    applying a first solution to the hydrophobic interaction chromatography material to produce a conditioned hydrophobic interaction chromatography material,
    applying a second solution comprising a polypeptide comprising a histidine-tag to the conditioned hydrophobic interaction chromatography material,
    optionally applying a third solution to the hydrophobic interaction chromatography material,
    recovering and thereby obtaining the polypeptide with a fourth solution comprising imidazole or an imidazole-derivative from the hydrophobic interaction chromatography material,
    whereby the first to third solutions are free of imidazole and imidazole-derivatives.

In the following different embodiments of all the aspects as reported before are presented.

In one embodiment the first solution comprises a first buffer substance, the second solution comprises a second buffer substance, the third solution comprises a third buffer substance, and the fourth solution comprises a fourth buffer substance, whereby the fourth buffer substance is imidazole or an imidazole derivative, with the proviso that at least the second buffer substance and the third buffer substance and the fourth buffer substance are all different buffer substances. In one embodiment the first solution and/or the second solution and/or the third solution is free of imidazole and imidazole-derivatives. In another embodiment the applying the first solution is for 3 to 20 column volumes. In another embodiment the applying the first solution is for 3 to 10 column volumes. In one embodiment the applying the second solution is for 1 to 10 column volumes. In another embodiment the applying the third solution is for 1 to 10 column volumes.

The hydrophobic interaction chromatography material is in the first step conditioned with a buffered solution. This solution does not comprise imidazole or an imidazole-derivative. The buffer substance of the conditioning, first buffer solution can be the same or different from the buffer substance of the second solution comprising the polypeptide comprising a histidine-tag.

Thereafter a second solution comprising the polypeptide comprising the histidine-tag is applied to the conditioned hydrophobic interaction chromatography material. In this step the polypeptide comprising the histidine-tag is retained on the hydrophobic interaction chromatography material. This solution does not comprise imidazole or an imidazole-derivative. The buffer substance of the loading, i.e. second, buffer solution can be the same or different from the buffer substance of the third solution.

After the loading of the chromatography material with the polypeptide comprising a histidine-tag optionally a washing, i.e. third, solution can be applied to the loaded hydrophobic interaction chromatography material. This solution does not comprise imidazole or an imidazole-derivative.

Finally for recovering the polypeptide comprising a histidine-tag from the hydrophobic interaction chromatography material a recovering, i.e. fourth, solution comprising imidazole or an imidazole-derivative is applied to the chromatography material.

In one embodiment the method for purifying or obtaining a polypeptide comprising a histidine-tag is a column chromatography method.

The volume applied to the hydrophobic interaction chromatography material in the different steps is independently of each other of from 3 to 20 column volumes, in one embodiment of from 4 to 10 column volumes. In one embodiment the conductivity of the first solution is the same or higher than the conductivity of the second solution comprising a polypeptide comprising a histidine-tag and/or than the conductivity of the third solution and/or the conductivity of the fourth solution.

The pH value of the solutions in the method as reported herein is of from pH 5 to pH 8. The method as reported herein is exemplified in the Examples with a conjugate of insulin-like growth factor-1 and a histidine-tag. The preparation thereof is reported e.g. in WO 2008/025527 (incorporated herein by reference). This data is presented solely in order to exemplify the current method and has not to be treated as a limitation of the current invention.

The following examples and figures are provided to aid the understanding of the present invention, the true scope of which is set forth in the appended claims. It is understood that modifications can be made in the procedures set forth without departing from the spirit of the invention.

EXAMPLE 1

Material and Methods

Figure 1:
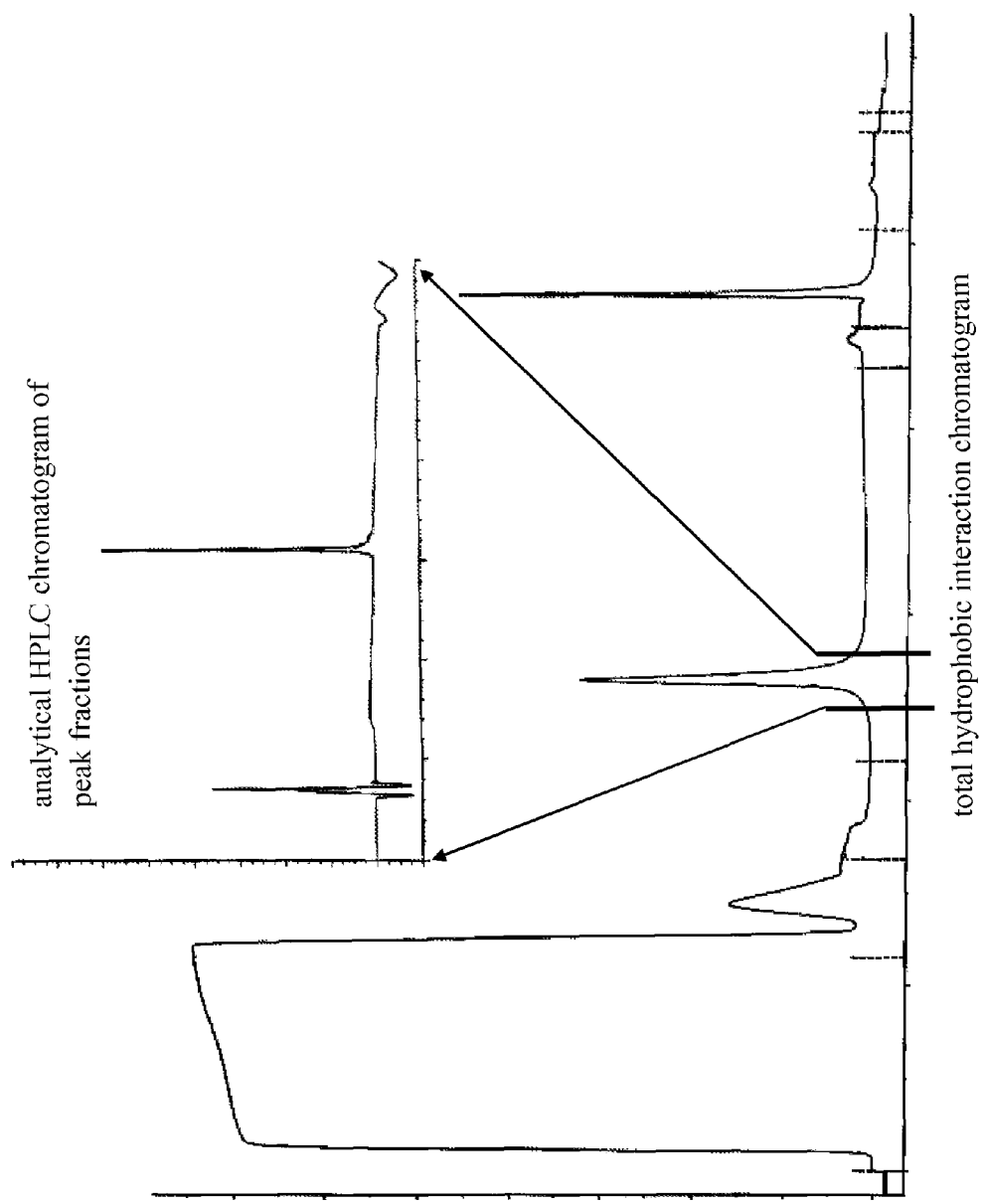
FIG. 1 Total hydrophobic interaction material (poly (propylene glycol) ligand) elution chromatogram for a method as reported herein with an elution with 20 mM imidazole by a linear gradient to 100% elution-buffer in 10 column volumes; small image: analytical HPLC chromatogram of the combined peak fractions.

If not otherwise indicated have the different chromatography methods been performed according to the chromatography material manufacturer's manual.

Recombinant DNA Techniques:

Standard methods were used to manipulate DNA as described in Sambrook, J., et al., Molecular cloning: A laboratory manual; Cold Spring Harbor Laboratory Press, Cold Spring Harbor, N.Y., 1989. The molecular biological reagents were used according to the manufacturer's instructions.

Protein Determination:

Protein concentration was determined by determining the optical density (OD) at 280 nm, with a reference wavelength of 320 nm, using the molar extinction coefficient calculated on the basis of the amino acid sequence.

Size-Exclusion-HPLC:

The chromatography was conducted with a Tosoh Haas TSK 3000 SWXL column on an ASI-100 HPLC system (Dionex, Idstein, Germany). The elution peaks were monitored at 280 nm by a UV diode array detector (Dionex). After dissolution of the concentrated samples to 1 mg/ml the column was washed with a buffer consisting of 200 mM potassium dihydrogen phosphate and 250 mM potassium chloride pH 7.0 until a stable baseline was achieved. The analyzing runs were performed under isocratic conditions using a flow rate of 0.5 ml/min. over 30 min. at room temperature. The chromatograms were integrated manually with Chromeleon (Dionex, Idstein, Germany).

Reversed Phase HPLC (RP-HPLC):

The purity is analyzed by RP-HPLC. The assay is performed on a Phenomenex C18 column using an acetonitrile/aqueous TFA gradient. The elution profile is monitored as UV absorbance at 215 nm. The percentages of the eluted substances are calculated based upon the total peak area of the eluted proteins.

DNA-Threshold-System:

See e.g. Merrick, H., and Hawlitschek, G., Biotech Forum Europe 9 (1992) 398-403.

Host Cell Protein Determination:

The walls of the wells of a micro titer plate are coated with a mixture of serum albumin and Streptavidin. A goat derived polyclonal antibody against HCP is bound to the walls of the wells of the micro titer plate. After a washing step different wells of the micro titer plate are incubated with a HCP calibration sequence of different concentrations and sample solution. After the incubation not bound sample material is removed by washing with buffer solution. For the detection the wells are incubated with an antibody peroxidase conjugate to detect bound host cell protein. The fixed peroxidase activity is detected by incubation with ABTS and detection at 405 nm.

DNA Determination:

Biotin was bound to a microtiter plate. A reaction mixture of streptavidin, single-stranded DNA and biotinylated single-stranded DNA binding protein was added. The binding protein was able to bind DNA and was biotinylated. In this manner it was possible to specifically remove the DNA from the sample mixture. The streptavidin bound the biotin on the microtiter plate as well as the biotin which was coupled to the single-stranded DNA binding protein. A DNA-specific antibody which was coupled to urease was added to this total complex. Addition of urea resulted in a hydrolysis of the urea which caused a local change in the pH. This change can be detected as an altered surface potential. The change in the surface potential was proportional to the amount of bound DNA. Single stranded DNA was obtained by proteinase K digestion and denaturation with SDS.

General Method for the Isolation, Solubilization and Re-Folding of Polypeptide from Inclusion Bodies:

In addition to the method performed in the cited literature can the preparation of inclusion bodies e.g. be performed according the method by Rudolph et al. (Rudolph, R., et al., Folding Proteins, In: T. E. Creighton (ed.): Protein function: A Practical Approach, 57-99 (1997)). The inclusion bodies were stored at −70° C. Solubilization of the inclusion bodies can likewise be performed according the method by Rudolph et al. (Rudolph, R., et al., Folding Proteins, In: T. E. Creighton (ed.): Protein function: A Practical Approach (1997) 57-99).

EXAMPLE 2

Figure 2:
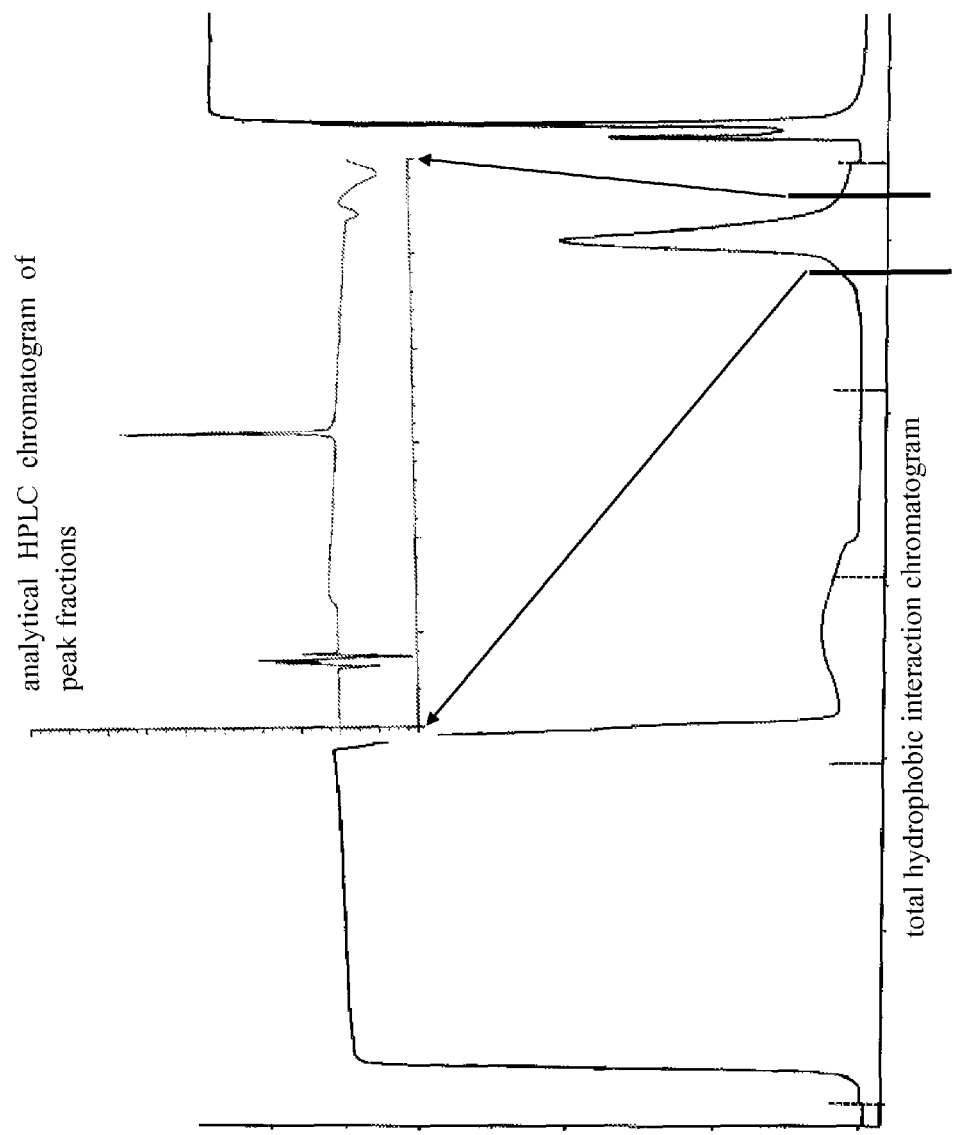
FIG. 2 Total hydrophobic interaction material (poly (propylene glycol) ligand) elution chromatogram for a method as reported herein with an elution with 20 mM imidazole by a linear gradient to 50% elution-buffer in 10 column volumes; small image: analytical HPLC chromatogram of the combined peak fractions.
Figure 3:
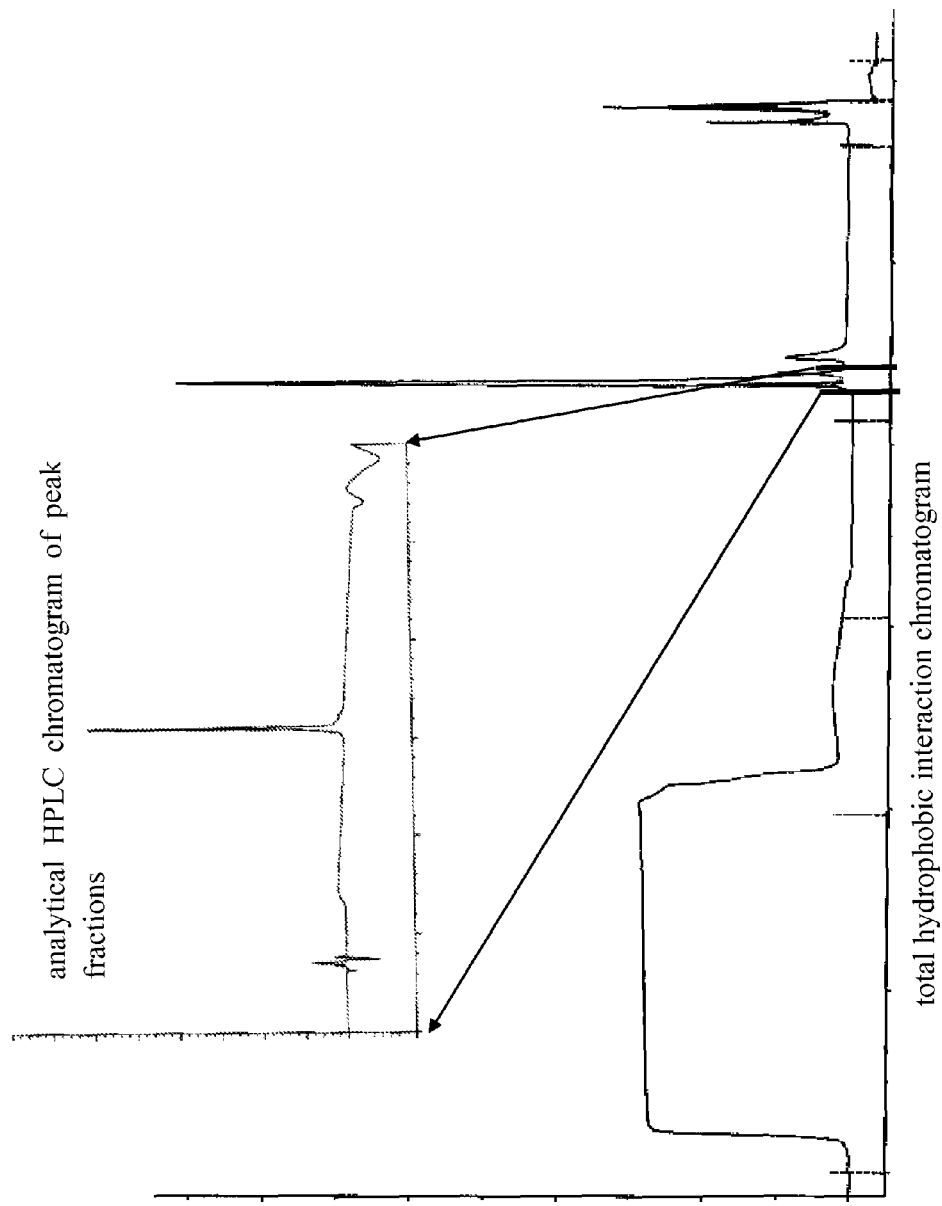
FIG. 3 Total hydrophobic interaction material (poly (propylene glycol) ligand) elution chromatogram for a method as reported herein with an elution with 20 mM imidazole by a step elution to 100% elution-buffer; small image: analytical HPLC of the combined peak fractions.

Purification of Histidine-Tagged-IGF-I on a Hydrophobic Interaction Chromatography Column with Imidazole Elution resin: TOYOPEARL® Polypropylenglycol-600; TOYOPEARL® PPG-600M (Tosoh Bioscience, Stuttgart, Germany)
load: a) 118 mg polypeptide
  b) 1034 mg polypeptide
  c) 1034 mg polypeptide
column dimension: a) 13 cm height, 11 ml bed volume
  b) 22 cm height, 108 ml bed volume
  c) 22 cm height, 108 ml bed volume
equilibration-buffer/first solution: 20 mM $KH_2PO_4$, 0.8 M NaCl, pH 3.5
wash-buffer 1/second solution: 1M TRIS-HCl, 0.15 M NaCl, pH 3.5
wash-buffer 2/third solution: 20 mM $KH_2PO_4$, 0.8 M NaCl, pH 3.5
elution-buffer/fourth solution: 20 mM imidazole, pH 9.7
elution-method: a) linear gradient to 100% elution-buffer in 20 column volumes
  b) linear gradient to 50% elution buffer in 10 column volumes
  c) step elution to 100% elution buffer
Result:
As can be seen from FIGS. 1 to 3 with any of the three employed elution methods the histidine-tagged-IGF-I molecule can be recovered from the poly (propylene glycol) hydrophobic interaction chromatography material.

EXAMPLE 3

Figure 4:
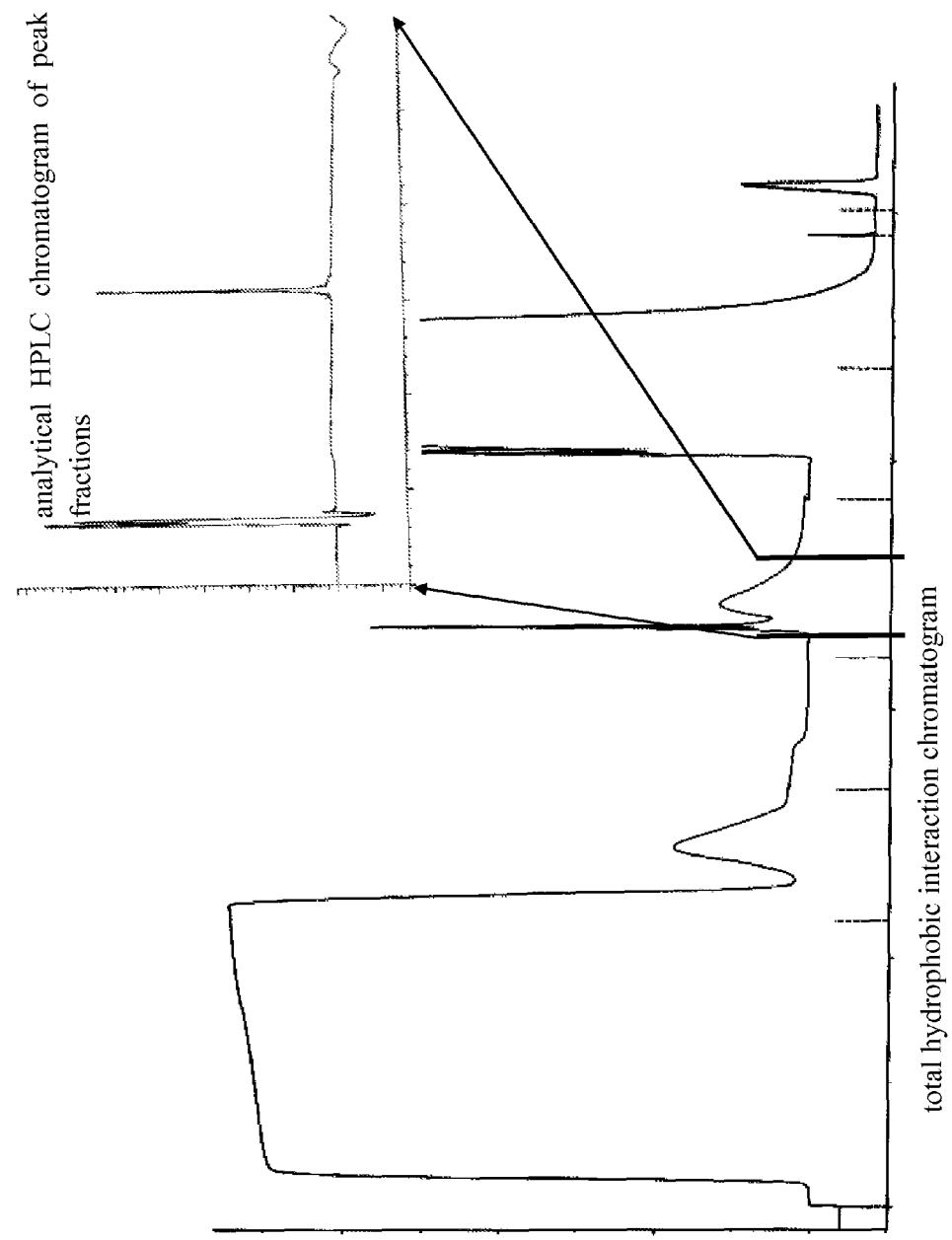
FIG. 4 Total hydrophobic interaction material (poly (propylene glycol) ligand) elution chromatogram for a method as reported herein with an elution with 100 mM histidine by a linear gradient to 100% elution-buffer in 20 column volumes; small image: analytical HPLC chromatogram of the combined peak fractions.
Figure 5:
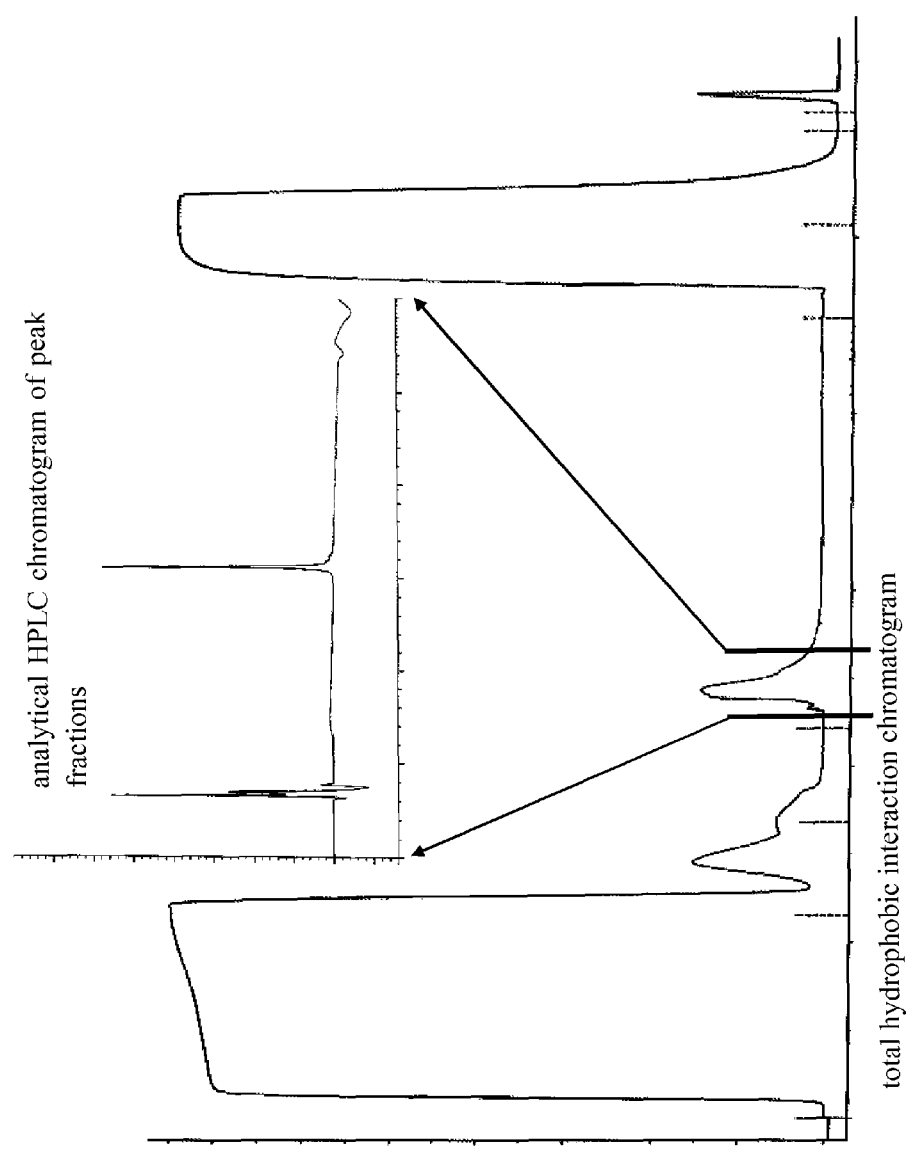
FIG. 5 Total hydrophobic interaction material (poly (propylene glycol) ligand) elution chromatogram for a method as reported herein with an elution with 20 mM histidine by a linear gradient to 100% elution-buffer in 20 column volumes; small image: analytical HPLC of the combined peak fractions.

Purification of Histidine-Tagged-IGF-I on a Hydrophobic Interaction Chromatography Column with Histidine Elution resin: TOYOPEARL® Polypropylenglycol-600; TOYOPEARL® PPG-600M (Tosoh Bioscience, Stuttgart, Germany)
load: 123 mg polypeptide
column dimension: 13 cm height, 11 ml bed volume
equilibration-buffer/first solution: 20 mM $KH_2PO_4$, 0.8 M NaCl, pH 3.5
wash-buffer 1/second solution: 1M TRIS-HCl, 0.15 M NaCl, pH 3.5
wash-buffer 2/third solution: 20 mM $KH_2PO_4$, 0.8 M NaCl, pH 3.5
elution-buffer/fourth solution: a) 100 mM histidine, pH 9.7 b) 20 mM histidine, pH 9.7
elution-method: linear gradient to 100% elution-buffer in 20 column volumes
Result:
As can be seen from FIGS. 4 and 5 with any of the two employed elution solutions the histidine-tagged-IGF-I molecule can be recovered from the poly (propylene glycol) hydrophobic interaction chromatography material.

EXAMPLE 4

Figure 6:
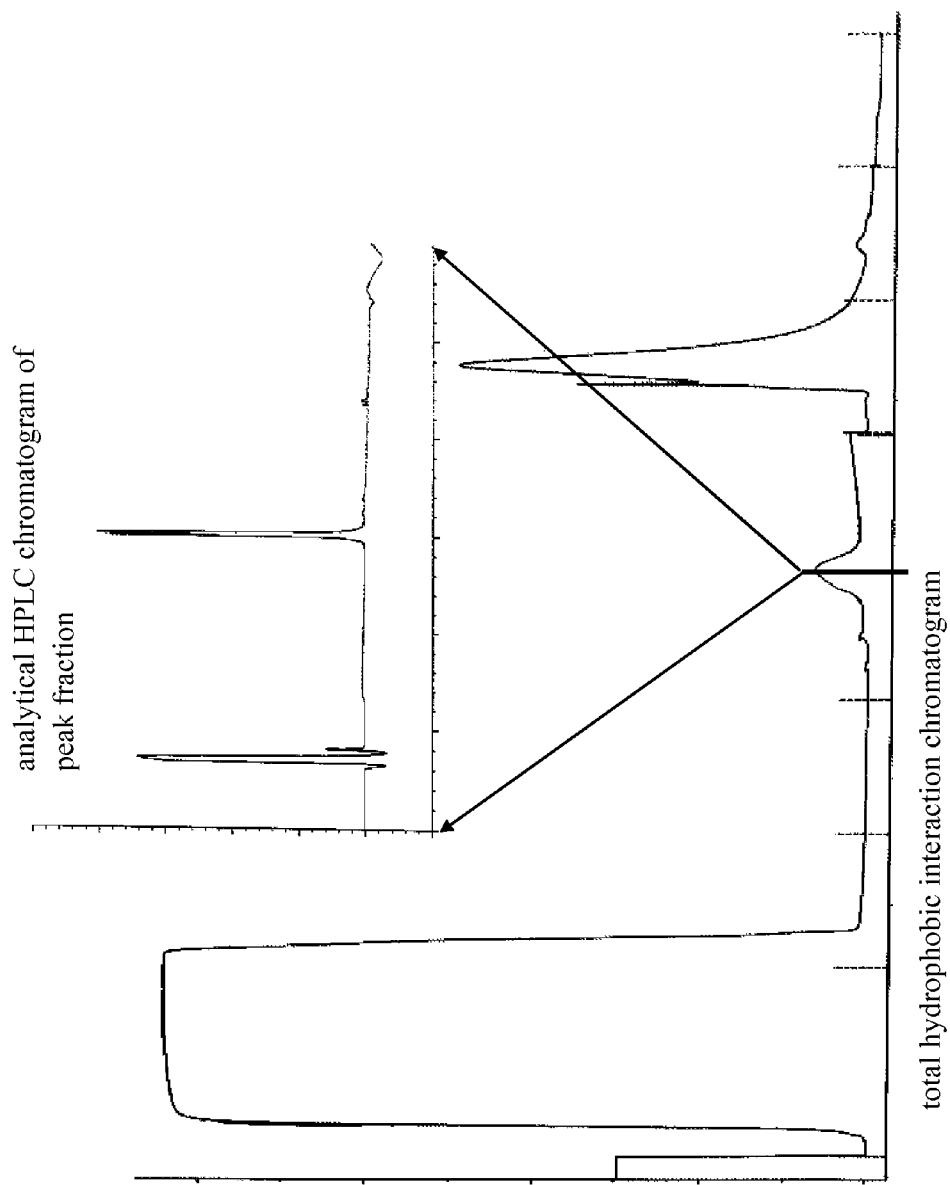
FIG. 6 Total hydrophobic interaction material (butyl ligand) elution chromatogram for a method as reported herein with an elution with 20 mM imidazole by a linear gradient to 50% elution-buffer in 10 column volumes; small image: analytical HPLC chromatogram of the peak fraction.

Purification of Histidine-Tagged-IGF-I on a Hydrophobic Interaction Chromatography Column with Imidazole Elution resin: Capto™ Butyl (GE Healthcare, Uppsala, Sweden)
load: 104 mg polypeptide
column dimension: 13.5 cm height, 10.7 ml bed volume
equilibration-buffer/first solution: 20 mM $KH_2PO_4$, 0.8 M NaCl, pH 3.5
wash-buffer 1/second solution: 1M TRIS-HCl, 0.35 M NaCl, 20 mM citric acid, pH 3.5
wash-buffer 2/third solution: 20 mM $KH_2PO_4$, 0.8 M NaCl, pH 3.5
elution-buffer/fourth solution: 20 mM imidazole, pH 9.7
elution-method: linear gradient to 50% elution-buffer in 10 column volumes
Result:
As can be seen from FIG. 6 histidine-tagged-IGF-I can be recovered with the elution buffer from the butyl hydrophobic interaction chromatography material.

EXAMPLE 5

Comparative Example

Figure 7:
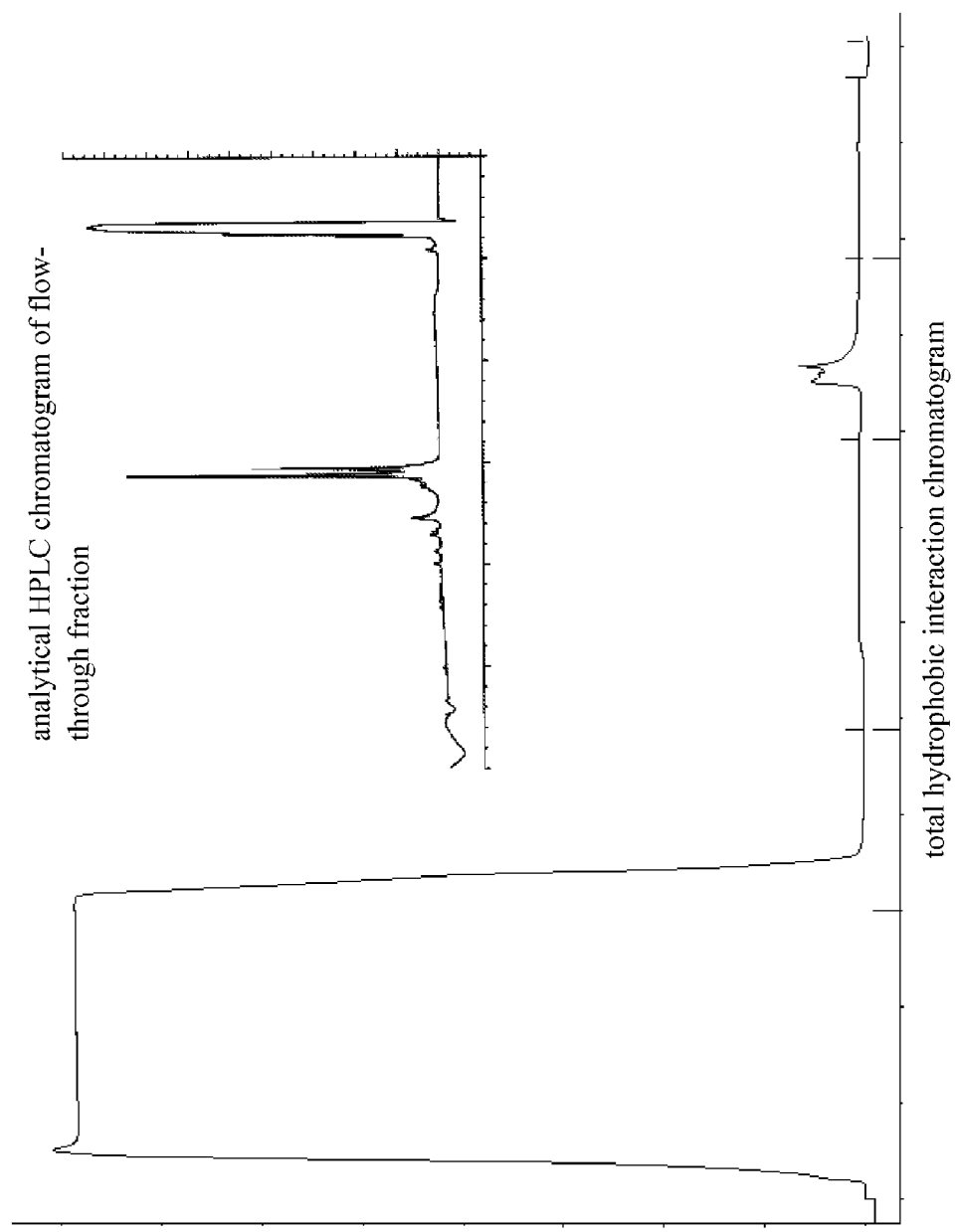
FIG. 7 Total hydrophobic interaction material (poly (propylene glycol) ligand) elution chromatogram with elution with 20 mM potassium phosphate buffer by a linear gradient to 50% elution-buffer in 10 column volumes; small image: analytical HPLC chromatogram of the flow-through fraction.

Purification of Histidine-Tagged-IGF-I on a Hydrophobic Interaction Chromatography Column with Phosphate Elution resin: TOYOPEARL® Ether-650M (Tosoh Bioscience, Stuttgart, Germany) load: 102 mg polypeptide
equilibration-buffer/first solution: 20 mM $KH_2PO_4$, 1M NaCl, pH 7.0
wash-buffer 1/second solution: 20 mM $KH_2PO_4$, 1M NaCl, pH 7.0
elution-buffer/fourth solution: 20 mM $KH_2PO_4$, pH 7.0
elution-method: step elution to 100% elution buffer
Result:
As can be seen from FIG. 7 the histidine-tagged-IGF-I molecule can not be recovered from the ether hydrophobic interaction chromatography material solely with a phosphate containing buffer.

EXAMPLE 6

Comparative Example

Figure 8:
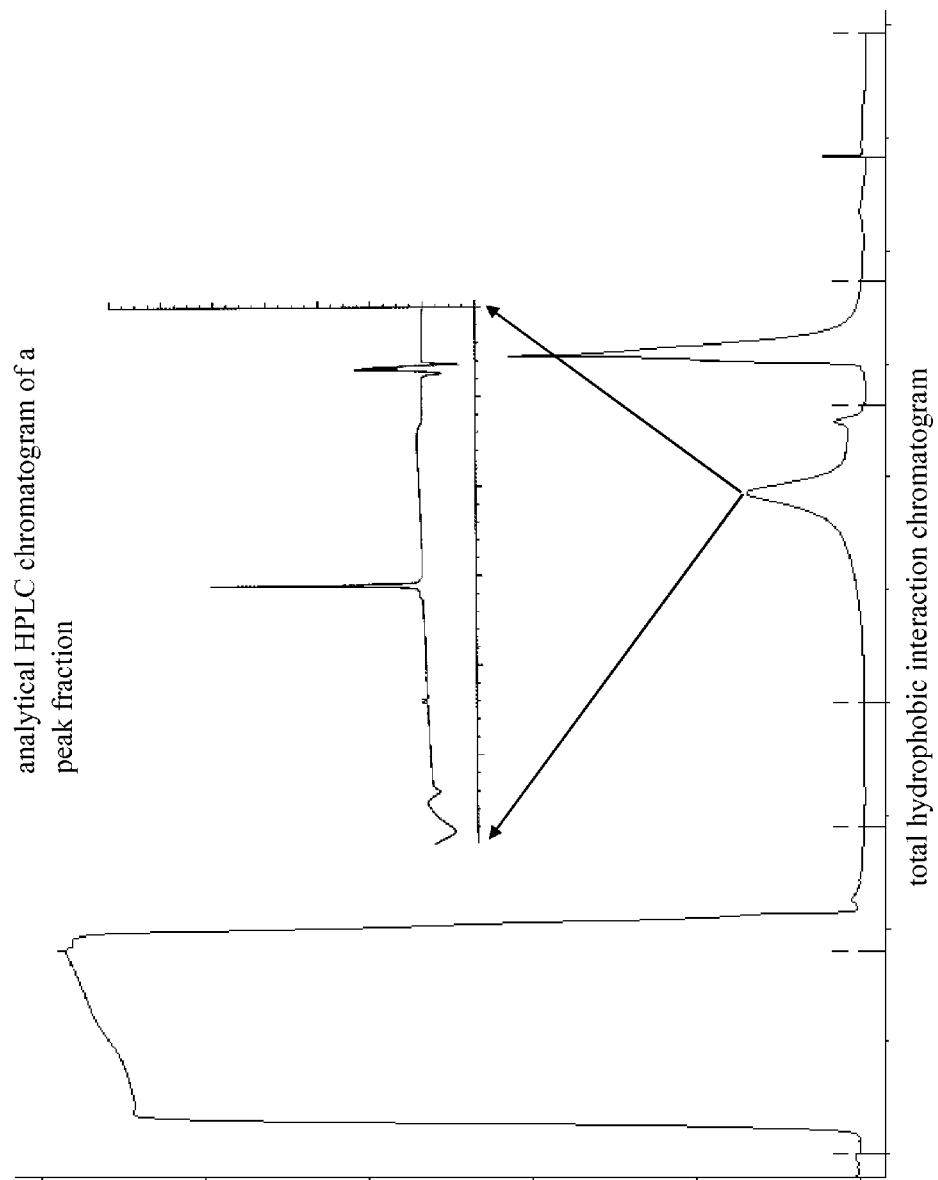
FIG. 8 Total hydrophobic interaction material (phenyl ligand) elution chromatogram for a method as reported herein with an elution with 5 mM imidazole by a linear gradient to 50% elution-buffer in 10 column volumes; small image: analytical HPLC chromatogram of a peak fraction.
Figure 9:
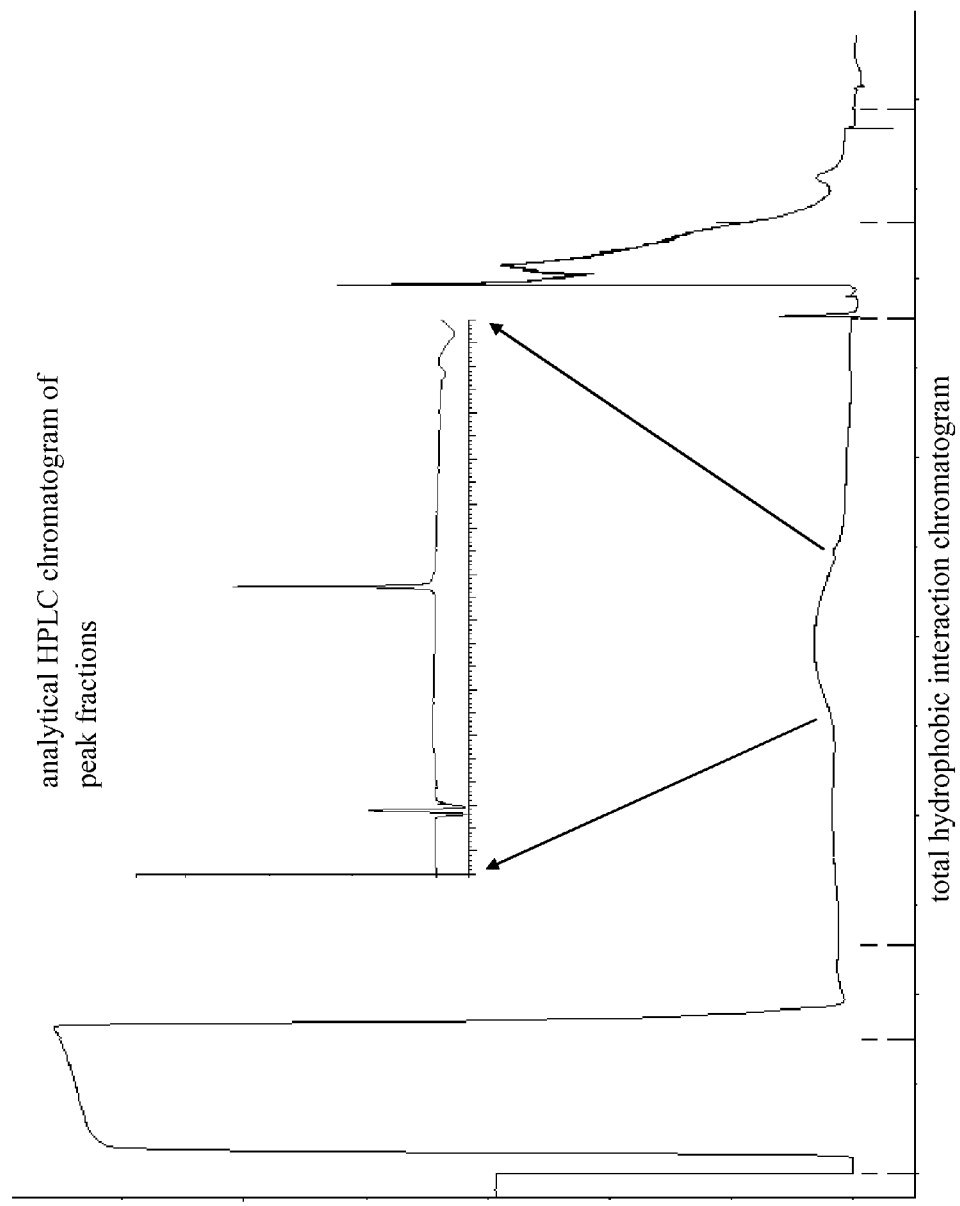
FIG. 9 Total hydrophobic interaction material (poly (propylene glycol) ligand) elution chromatogram for a method as reported herein with an elution with 1.5 M sodium chloride by a linear gradient to 100% elution-buffer in 30 column volumes; small image: analytical HPLC chromatogram of the combined peak fractions.

Purification of Histidine-Tagged-IGF-I on a Hydrophobic Interaction Chromatography Column with Different Elution resin: a) Phenyl Sepharose™ (GE Healthcare, Uppsala, Sweden)
  b) TOYOPEARL® PPG-600M (Tosoh Bioscience, Stuttgart, Germany)
load: 80 mg polypeptide
column dimension: 14 cm height, 11 ml bed volume
equilibration-buffer/first solution: a) 20 mM $KH_2PO_4$, 0.8 M NaCl, pH 3.5
  b) 20 mM $KH_2PO_4$, 1.5 M NaCl, pH 3.5
wash-buffer 1/second solution: a) 1M TRIS-HCl, 0.35 M NaCl, 20 mM citric acid, pH 3.5 b) —
wash-buffer 2/third solution: a) 20 mM $KH_2PO_4$, 0.8 M NaCl, pH 3.5
b) 20 mM $KH_2PO_4$, 1.5 M NaCl, pH 3.5
elution-buffer/fourth solution: a) 5 mM imidazole, 20% (v/v) 2-propanol, pH 7.0
b) 1.5 M NaCl, 20% (v/v) 2-propanol, pH 3.5
elution-method: a) linear gradient to 50% elution-buffer in 10 column volumes
b) linear gradient to 100% elution buffer in 30 column volumes
Result:
As can be seen from FIG. 8 histidine-tagged-IGF-I can be recovered with an imidazole and 2-propanol containing elution buffer from the phenyl Sepharose™ hydrophobic interaction chromatography material in a sharp peak. This cannot be achieved with an imidazole-free elution buffer (see FIG. 9).

EXAMPLE 7

Comparative Example

Figure 10:
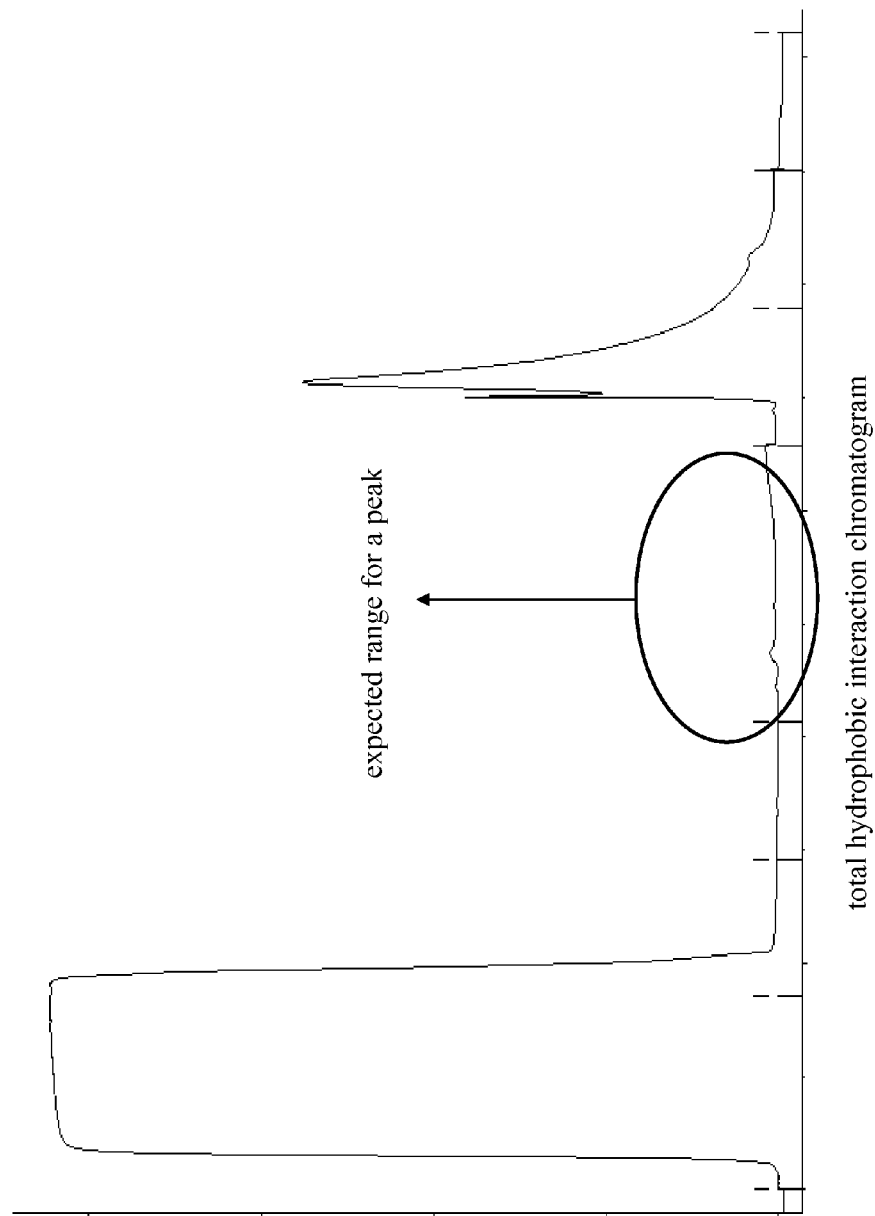
FIG. 10 Total hydrophobic interaction material (poly (propylene glycol) ligand) elution chromatogram for a method as reported herein with an elution with 20 mM imidazole by a linear gradient to 50% elution-buffer in 10 column volumes.

Purification of Histidine-Tagged-IGF-I on a Hydrophobic Interaction Chromatography Column with Imidazole Elution resin: Capto™ Phenyl (GE Healthcare, Uppsala, Sweden)
load: 117 mg polypeptide
column dimension: 13.5 cm height, 10.7 ml bed volume
equilibration-buffer/first solution: 20 mM $KH_2PO_4$, 0.8 M NaCl, pH 3.5
wash-buffer 1/second solution: 1M TRIS-HCl, 0.35 M NaCl, 20 mM citric acid, pH 3.5
wash-buffer 2/third solution: 20 mM $KH_2PO_4$, 0.8 M NaCl, pH 3.5
elution-buffer/fourth solution: 20 mM imidazole, pH 9.7 elution-method: linear gradient to 50% elution-buffer in 10 column volumes
Result:
As can be seen from FIG. 10 histidine-tagged-IGF-I cannot be recovered with the elution buffer from the phenyl hydrophobic interaction chromatography material.

EXAMPLE 8

Comparative Example

Figure 11:
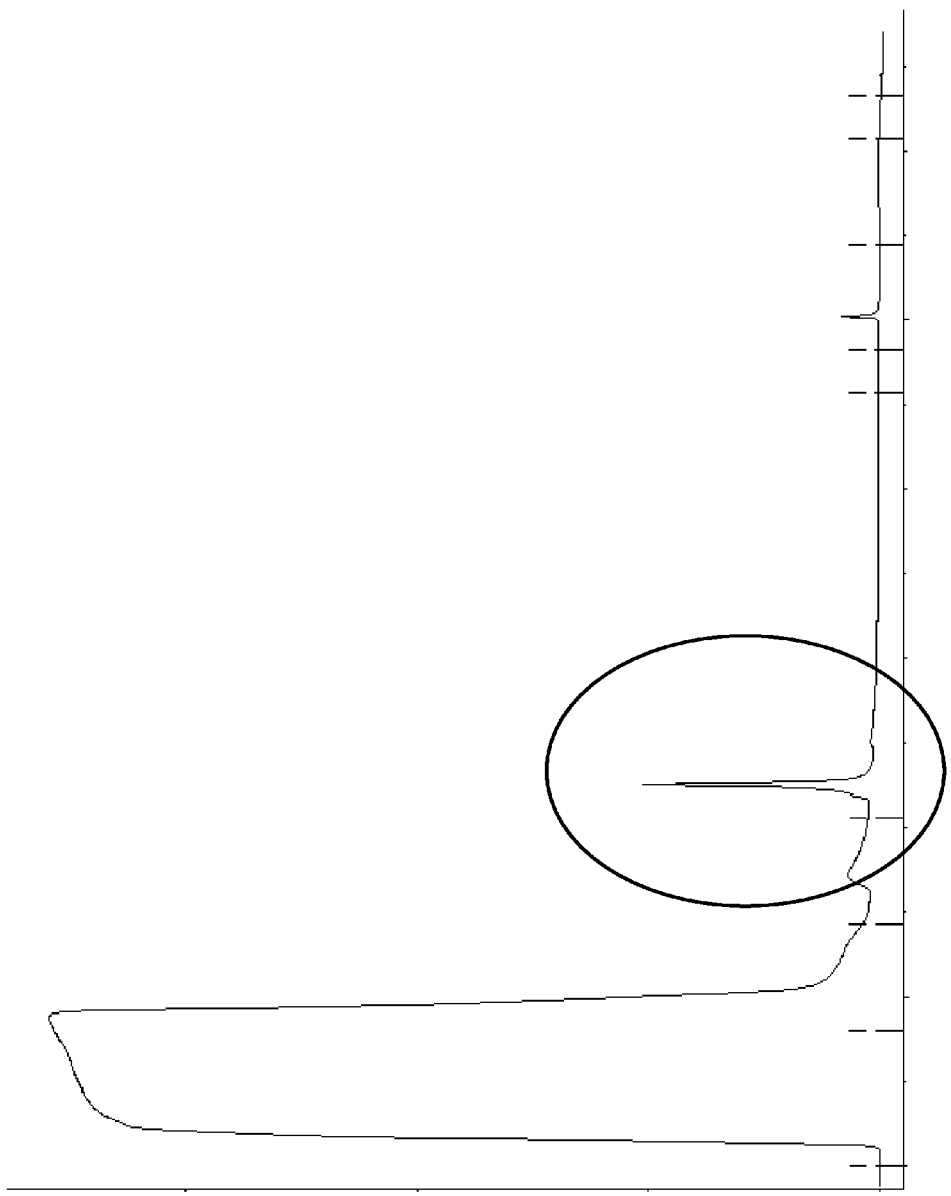
FIG. 11 Total hydrophobic interaction material (poly (propylene glycol) ligand) elution chromatogram for a method as reported herein with an elution with 20 mM potassium phosphate buffer by a linear gradient to 100% elution-buffer in 20 column volumes.

Purification of Herceptin® on a Hydrophobic Interaction Chromatography Column with Imidazole Elution The cultivation supernatant is adjusted to pH 3.5 and a NaCl concentration of 0.8 mol/l and filtrated through a Sartobran P filter prior to the application to the hydrophobic interaction chromatography material.
resin: TOYOPEARL® Polypropylenglycol-600; TOYOPEARL® PPG-600M (Tosoh Bioscience, Stuttgart, Germany)
load: 189 mg polypeptide
column dimension: 16 cm height, 12.6 ml bed volume
equilibration-buffer/first solution: 20 mM $KH_2PO_4$, 0.8 M NaCl, pH 3.5
wash-buffer 1/second solution: 1 M TRIS-HCl, 0.35 M NaCl, 20 mM citric acid, pH 3.5
elution-buffer/fourth solution: a) 20 mM imidazole, pH 9.7
b) 20 mM $KH_2PO_4$, pH 8.9
elution-method: a) linear gradient to 50% elution-buffer in 10 column volumes
b) linear gradient to 100% elution buffer in 20 column volumes
Result:
A fraction of Herceptin® can be found in the flow-through by imidazole elution. A further fraction can be recovered from the column as small peak at the beginning of the elution. In contrast thereto, as shown in FIG. 11, by an elution with a phosphate buffered solution Herceptin® can be obtained as a sharp peak.

The invention claimed is:

1. A method for purifying a polypeptide comprising a histidine-tag comprising the following steps:
applying a solution comprising the polypeptide with a histidine-tag to a hydrophobic interaction chromatography material, and
recovering the polypeptide comprising a histidine-tag with a solution comprising imidazole or an imidazole-derivative from the hydrophobic interaction chromatography material and thereby purifying the polypeptide comprising a histidine-tag.

2. A method for producing a polypeptide comprising a histidine-tag comprising the following steps:
cultivating a prokaryotic or eukaryotic cell comprising a nucleic acid encoding a polypeptide comprising a histidine-tag,
recovering the polypeptide comprising a histidine-tag from the cells or/and the cultivation medium,
purifying the polypeptide comprising a histidine-tag with a hydrophobic interaction chromatography method comprising the following steps:
applying a solution comprising the polypeptide with a histidine-tag to a hydrophobic interaction chromatography material, and
recovering the polypeptide comprising a histidine-tag with a solution comprising imidazole or an imidazole-derivative from the hydrophobic interaction chromatography material and thereby producing a polypeptide comprising a histidine-tag.

3. The method of claim 1, characterized in that the hydrophobic interaction chromatography material comprises a matrix of agarose to which a hydrophobic ligand has been attached.

4. The method of claim 3, characterized in that the ligand is a propyl-, butyl-, pentyl-, hexyl-, heptyl-, octyl-, poly(ethylene glycol)- or poly(propylene glycol)-ligand.

5. The method of claim 3, characterized in that the ligand is a phenyl-ligand and the solution in the recovering step comprises in addition 2-propanol.

6. A method for purifying a polypeptide comprising a histidine-tag comprising:
applying a first solution to a hydrophobic interaction chromatography material,
applying a second solution comprising the polypeptide comprising a histidine-tag to the hydrophobic interaction chromatography material,
optionally applying a third solution to the hydrophobic interaction chromatography, and
recovering and thereby producing or purifying the polypeptide comprising a histidine-tag with a fourth solution comprising imidazole or an imidazole-derivative,
wherein the first solution comprises a first buffer substance, the second solution comprises a second buffer substance, and the fourth solution comprises a fourth buffer substance, wherein the fourth buffer substance is imidazole or an imidazole derivative, and wherein further the second buffer substance and the fourth buffer substance are different buffer substances.

7. The method of claim 6 comprising, after applying the second solution and prior to recovering and purifying the polypeptide, the following step:

applying a third solution to the hydrophobic interaction chromatography material, wherein the third solution comprises a third buffer substance, wherein further the second buffer substance, and the third buffer substance, and the fourth buffer substance are all different buffer substances.

8. The method of claim 2, wherein the hydrophobic interaction chromatography material comprises a matrix of agarose to which a hydrophobic ligand has been attached.

9. The method of claim 8, characterized in that the ligand is a propyl-, butyl-, pentyl-, hexyl-, heptyl-, octyl-, poly(ethylene glycol)- or poly(propylene glycol)-ligand.

10. The method of claim 8, characterized in that the ligand is a phenyl-ligand and the solution in the recovering step comprises in addition 2-propanol.

11. A method for producing a polypeptide comprising a histidine-tag comprising:

cultivating a prokaryotic or eukaryotic cell comprising a nucleic acid encoding a polypeptide comprising a histidine-tag, recovering the polypeptide comprising a histidine-tag from the cells or/and the cultivation medium, purifying the polypeptide comprising a histidine-tag with a hydrophobic interaction chromatography method comprising:

applying a first solution to a hydrophobic interaction chromatography material, applying a second solution comprising the polypeptide comprising a histidine-tag to the hydrophobic interaction chromatography material, optionally applying a third solution to the hydrophobic interaction chromatography, and recovering and thereby producing or purifying the polypeptide comprising a histidine-tag with a fourth solution comprising imidazole or an imidazole-derivative, wherein the first solution comprises a first buffer substance, the second solution comprises a second buffer substance, and the fourth solution comprises a fourth buffer substance, wherein the fourth buffer substance is imidazole or an imidazole derivative, and wherein further the second buffer substance and the fourth buffer substance are different buffer substances.

12. The method of claim 11 comprising, after applying the second solution and prior to recovering and purifying the polypeptide, the following step:

applying a third solution to the hydrophobic interaction chromatography material, wherein the third solution comprises a third buffer substance, wherein further the second buffer substance, and the third buffer substance, and the fourth buffer substance are all different buffer substances.

* * * * *